United States Patent
Hutchison

(10) Patent No.: US 10,064,756 B2
(45) Date of Patent: Sep. 4, 2018

(54) SYSTEM AND METHOD FOR PROVIDING RADIATION HAVING ANNULAR PROFILE

(71) Applicant: Topcon Medical Laser Systems, Inc, Santa Clara, CA (US)

(72) Inventor: Sheldon Hutchison, Sunnyvale, CA (US)

(73) Assignee: TOPCON MEDICAL LASER SYSTEMS, INC., Santa Clara, CA (US)

( * ) Notice: Subject to any disclaimer, the term of this patent is extended or adjusted under 35 U.S.C. 154(b) by 723 days.

(21) Appl. No.: 14/152,190

(22) Filed: Jan. 10, 2014

(65) Prior Publication Data

US 2015/0196427 A1  Jul. 16, 2015

(51) Int. Cl.
| | | |
|---|---|---|
| G02B 13/00 | (2006.01) | |
| A61F 9/008 | (2006.01) | |
| G02B 3/08 | (2006.01) | |
| G02B 27/09 | (2006.01) | |
| A61B 3/00 | (2006.01) | |
| A61B 3/135 | (2006.01) | |
| A61F 9/009 | (2006.01) | |

(52) U.S. Cl.
CPC ........ *A61F 9/00823* (2013.01); *A61B 3/0008* (2013.01); *A61B 3/135* (2013.01); *A61F 9/00821* (2013.01); *G02B 3/08* (2013.01); *G02B 27/0927* (2013.01); *G02B 27/0955* (2013.01); *A61F 9/009* (2013.01); *A61F 2009/00863* (2013.01)

(58) Field of Classification Search
CPC .. A61F 9/00823; A61F 9/00821; A61F 9/009; A61F 2009/00863; A61B 3/135; A61B 3/0008; G02B 27/0955; G02B 27/0927; G02B 3/08; G03F 7/0075; G03F 7/70233; G03F 7/70091; G03F 7/7015; G03F 7/70116
See application file for complete search history.

(56) References Cited

U.S. PATENT DOCUMENTS

| | | | |
|---|---|---|---|
| 4,842,393 A | 6/1989 | Gorman et al. | |
| 4,961,622 A * | 10/1990 | Gorman | G02B 3/04 359/708 |

(Continued)

FOREIGN PATENT DOCUMENTS

JP  2007173649 A  7/2007

OTHER PUBLICATIONS

Ilya Golub, Fresnel Axicon, Jun. 15 2006, Optics Letters, vol. 31. No. 12; pp. 1890-1892.*

(Continued)

*Primary Examiner* — Alicia M Harrington
(74) *Attorney, Agent, or Firm* — Chiesa Shahinian & Giantomasi PC

(57) ABSTRACT

A system includes a focusing element configured to receive electromagnetic radiation coaxially and to focus the electromagnetic radiation to generate focused radiation. The system also includes a refracting element having an associated focal plane. The refracting element is configured to receive the focused radiation, and to refract the focused radiation to produce refracted radiation having an annular pattern at the focal plane. The system also includes a slit lamp having a receiving element to receive the refracted radiation.

13 Claims, 6 Drawing Sheets

(56) References Cited

U.S. PATENT DOCUMENTS

| | | | | |
|---|---|---|---|---|
| 6,452,731 | B1* | 9/2002 | Schorning | B60R 1/001 |
| | | | | 359/619 |
| 8,336,555 | B2* | 12/2012 | Palanker | A61F 9/008 |
| | | | | 128/898 |
| 2010/0168724 | A1 | 7/2010 | Sramek et al. | |
| 2013/0272653 | A1 | 10/2013 | Le et al. | |

OTHER PUBLICATIONS

International Search Report and Written Opinion dated Mar. 31, 2015, in connection with International Patent Application No. PCT/US2015/010007, 10 pgs.

Lizotte, "Axicons, Prisms and Integrators: Searching for Simple Laser Beam Shaping Solutions," Laser Beam Shaping XI, Proc. of SPIE vol. 7789, Aug. 16, 2010, pp. 778902-1-778902-8.

Qiushi et al., Axicon: A New Laser Beam Delivery System for Corneal Surgery, IEEE Journal of Quantum Electronics vol. 26, No. 12, Dec. 1, 1990, pp. 2305-2308.

* cited by examiner

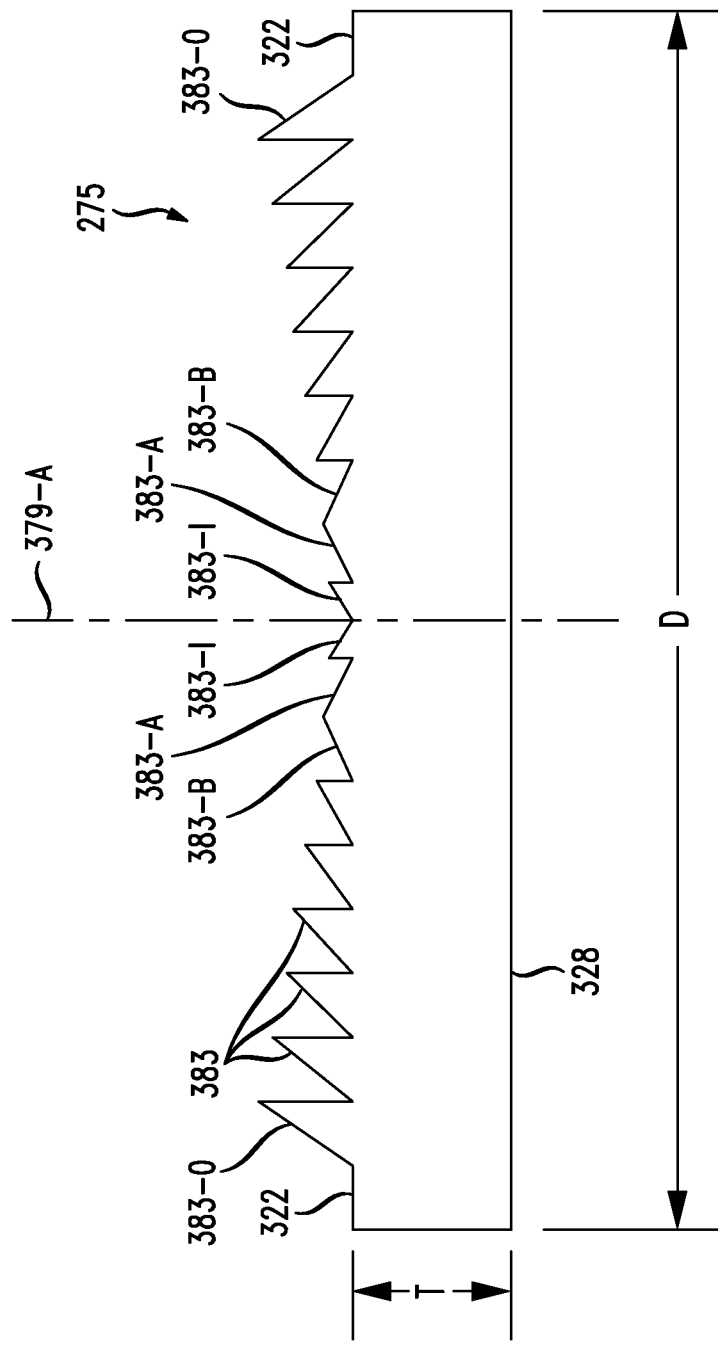

SYSTEM AND METHOD FOR PROVIDING RADIATION HAVING ANNULAR PROFILE

TECHNICAL FIELD

This specification relates generally to laser delivery systems and methods for use in diagnosing and treating conditions of the eye, and more particularly to laser delivery systems and methods for use with slit lamps or other imaging devices or other imaging devices.

BACKGROUND

Laser treatment has been employed for many years in treating conditions of the eye. For example, application of a laser to a target zone defined on selected tissue can be used to generate an elevated level of energy within the target zone, sufficient to coagulate the tissue. In one common application, photocoagulation of the retina is the standard of care for several retinopathies. In photocoagulation, it is important to deliver the correct dose of energy to the treated locations. Doses that are too small will have little or no therapeutic effect, while doses that are too large can rupture or otherwise damage the retina.

SUMMARY

In accordance with an embodiment, a system includes a focusing element that receives electromagnetic radiation coaxially and focuses the electromagnetic radiation to generate focused radiation. The system also includes a refracting element having an associated focal plane. The refracting element receives the focused radiation, and refracts the focused radiation to produce refracted radiation having an annular pattern at the focal plane. The system also includes a laser delivery system having a receiving element configured to receive the refracted radiation. The laser delivery system may be a slit lamp, for example.

In one embodiment, the system also includes an electromagnetic radiation source. The system may also include a fiber having a first end and a second end. The fiber receives the focused radiation emitted by the focusing element via the first end and emits the focused radiation via the second end. The refracting element receives the focused radiation emitted via the second end.

In another embodiment, the refracting element has a first surface, and a second surface comprising a plurality of facets arranged concentrically around a center of the second surface. Each of the plurality of facets has a respective height, and the heights of the facets varies based on a distance from the center of the second surface.

In another embodiment, a first facet has a first sloping surface, a first vertical surface, and a first facet angle associated with a first angle between the first sloping surface and the first vertical surface. The first facet angle is positive. A second facet has a second sloping surface, a second vertical surface, and a second facet angle associated with a second angle between the second sloping surface and the second vertical surface. The second facet angle is negative.

In another embodiment, an imaging system comprises a first lens that receives input light coaxially and focuses the light to produce focused light. The imaging system also includes a second lens having an associated focal plane. The second lens refracts the focused light to produce refracted light having an annular illumination pattern at the focal plane.

In another embodiment, the imaging system includes a slit lamp configured to receive the refracted light. The slit lamp may have an optical element that receives the refracted light at the focal plane. The imaging system may also include a light source.

In accordance with another embodiment, a method is provided. Electromagnetic radiation is received coaxially, by a focusing element. The electromagnetic radiation is focused to generate focused radiation. A refracting element receives the focused radiation, and refracts the focused radiation to produce refracted radiation having an annular pattern at a focal plane associated with the refracting element. The refracted radiation is provided to a laser delivery system.

These and other advantages of the present disclosure will be apparent to those of ordinary skill in the art by reference to the following Detailed Description and the accompanying drawings.

BRIEF DESCRIPTION OF THE DRAWINGS

FIG. 3B shows a cross-section of the output lens of FIG. 3A;

DETAILED DESCRIPTION

Figure 1:
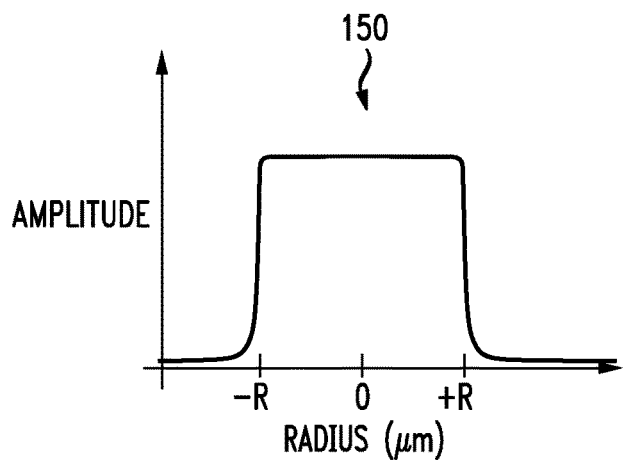
FIG. 1 shows a desired temperature profile across a target zone.

Laser treatment is commonly used to treat conditions of the eye. It is generally desirable to deliver a consistent, uniform dose of energy to the target zone of tissue, which may be a portion of the retina, for example. Accordingly, laser treatment is often employed to produce a desired temperature within a selected target zone of tissue. FIG. 1 shows a desired temperature profile 150 across a target zone defined by radius R. In the illustrative example, the target zone has a radius measured in microns. A uniform temperature profile such as that shown in FIG. 1 is sometimes referred to as a top-hat temperature profile.

Current laser treatment systems typically fail to produce a top-hat temperature profile in the irradiated zone, even if a laser having a top hat beam profile is applied. When a uniform beam profile is utilized to deliver this energy, thermal interaction with tissue can create an uneven, non-uniform interaction with the tissue. Due to more rapid heat diffusion from the periphery of an irradiated zone than from its center, the central part of an irradiated zone often has a higher temperature. There is a need for improved systems and methods capable of counteracting heat diffusion in order to achieve a constant temperature across a significant part of the irradiated zone. It would be preferable to produce across the irradiated zone a temperature profile that approximates a flat (top-hat) profile.

It has been observed that using an annular or ring-shaped illumination pattern in laser treatment can produce a temperature profile in the target zone that approximates a top-hat profile. Several existing systems and methods for photothermal therapy are described in U.S. Patent Publication No. 2010/0168724 to Sramek, dated Jul. 1, 2010 and entitled "Method and Apparatus for Photothermal Therapy with Adjustable Spatial and/or Temporal Beam Profile" (hereinafter referred to as "Sramek"). Sramek achieves a ring-shaped illumination pattern by coupling a laser beam into a fiber end-face at an acute angle with respect to normal incidence. However, due to the need to provide the input beam at an acute angle, it can be difficult to control the shape of the input laser beam in a system such as that disclosed by Sramek. There is a need for improved systems and methods that are capable of producing an annular, or ring-shaped, illumination pattern, thereby counteracting heat diffusion, and that allow greater control over the shape of the input laser beam than existing systems.

Figure 2:
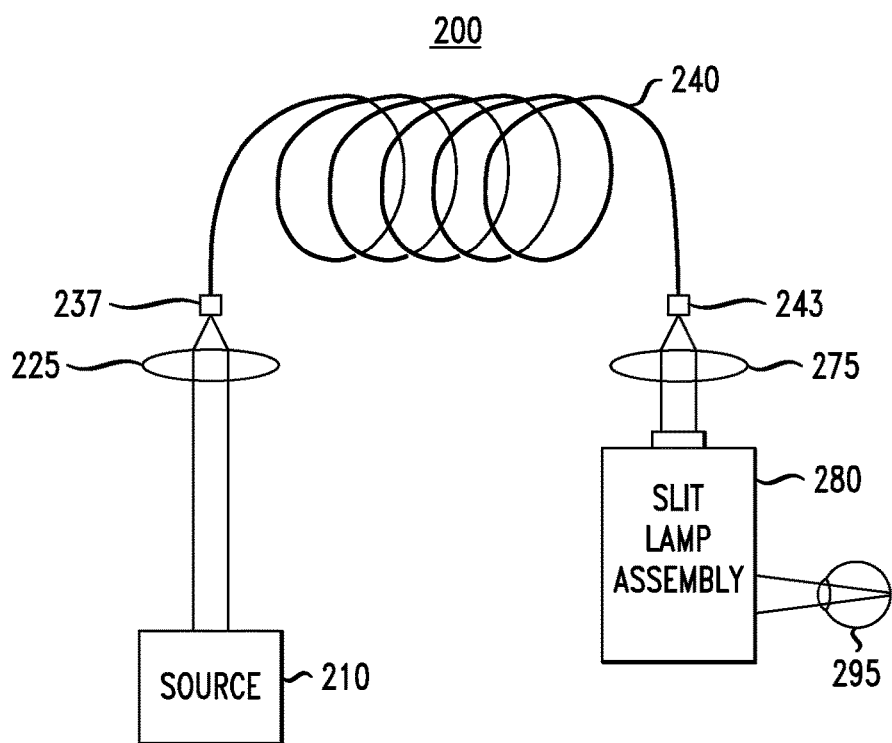
FIG. 2 shows a laser treatment delivery system in accordance with an embodiment.

FIG. 2 shows a laser treatment delivery system in accordance with an embodiment. System 200 comprises an electromagnetic radiation source 210, an input lens 225, a multi-mode fiber 240, an output lens 275, and a slit lamp assembly 280. Multi-mode fiber 240 includes a first fiber-end face 237 and a second fiber-end face 243.

In accordance with an embodiment, electromagnetic radiation source 210 emits radiation, which is focused by input lens 225. For example, electromagnetic radiation source 210 may emit laser light, monochromatic light, etc. In the embodiment of FIG. 2, radiation emitted by electromagnetic radiation source 210 is received by input lens 225 coaxially.

Input lens 225 may be any type of suitable lens. For example, input lens 225 may comprise glass, silica, silica substrate, etc.

Advantageously, input lens 225 receives radiation coaxially, in contrast to receiving radiation at a selected acute input angle, as is necessary in existing systems. For example, the system described by Sramek receives radiation at a selected acute input angle. Receiving radiation coaxially advantageously provides more control over the shape of the beam of radiation that enters and is transmitted through fiber 240, and consequently provides more control over the shape of the beam of radiation that enters slit lamp assembly 280 and is applied to the patient's eye. A system such as system 200 of FIG. 2, in which the input lens receives radiation coaxially, is therefore preferable to existing systems which receive radiation at an acute input angle.

Radiation focused by input lens 225 is received at fiber-end face 237 of multi-mode fiber 240. Fiber 240 transmits the radiation to, and emits the radiation via second fiber-end face 243.

Radiation emitted from second fiber-end face 243 of fiber 240 is received and focused by output lens 275, and received by slit-lamp assembly 280, which collimates, directs, and focuses the radiation to a desired location in a patient's eye 295. In particular, the light emitted by output lens 275 is received and used by slit lamp assembly 280 to irradiate a target zone within eye 295.

The light emitted by output lens 275 advantageously has a desired annular profile at a focal plane associated with output lens 275. An element of slit lamp assembly 280, such as a lens or mirror, may be disposed to receive the radiation at the focal plane. Advantageously, the annular profile of the light emitted by output lens 275 produces a desired temperature profile in the target zone.

Slit lamp assembly 280 may be any suitable slit lamp, microscope or other laser delivery system or device. Slit lamps are known. For example, slit lamp assembly 280 may be a SL-D7 slit lamp manufactured by Topcon Corporation, located in Tokyo, Japan. Alternatively, other slit lamps may be used, such as a Topcon SL-D3 slit lamp, a Topcon SL-D4 slit lamp, a Topcon OMS-710 surgical microscope, a Topcon Laser Indirect Ophthalmoscope, etc. Other delivery devices or systems may be used.

Figure 3A:
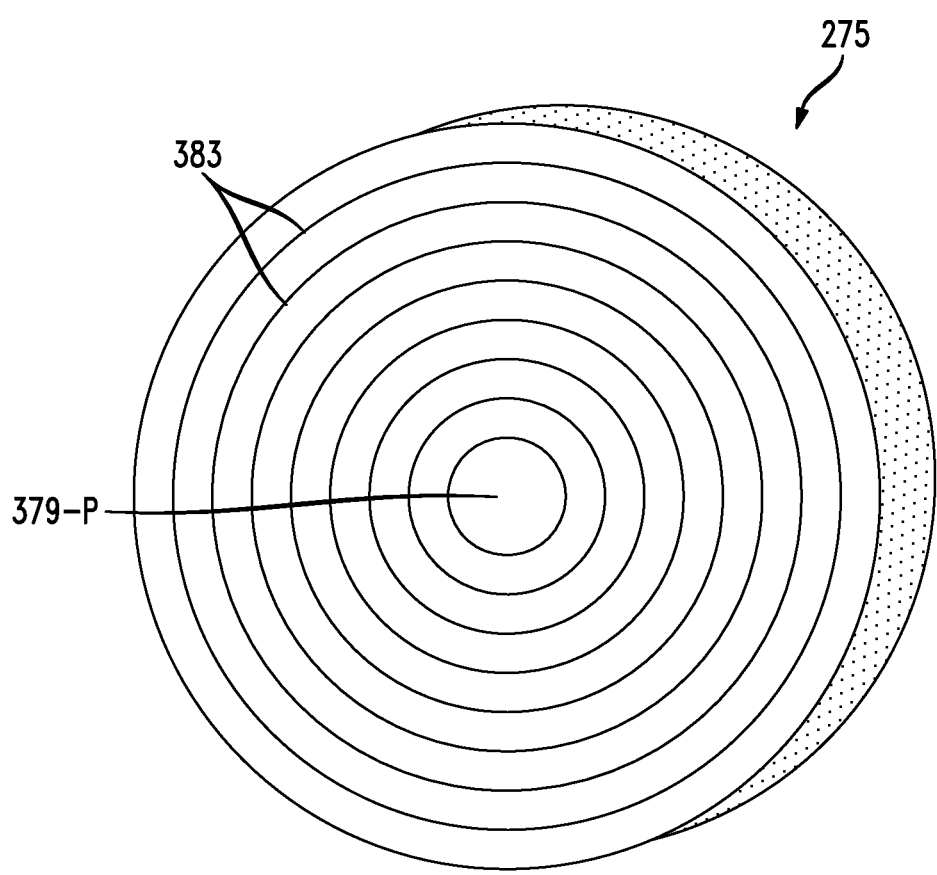
FIG. 3A shows an output lens in accordance with an embodiment.

FIG. 3A shows output lens 275 in accordance with an embodiment. Output lens 275 comprises a transmissive material such as glass, silica, silica substrate, etc. In other embodiments, output lens 275 may comprise other types of material. In other embodiments, output lens 275 may have a different shape than that shown in FIG. 3A.

In one embodiment, output lens 275 comprises a series of concentric facets 383 similar to those of a Fresnel lens. Fresnel lenses are known. In the embodiment of FIG. 3A, facets 383 are arranged concentrically around a central axis associated with a central point 379-P of output lens 275. In other embodiments, facets 383 may be arranged differently. Facets 383 refract incoming radiation to a form a defined annular shape on a focal plane located a defined distance from output lens 275.

Output lens 275 differs from a Fresnel lens. A Fresnel lens commonly focuses most or all incoming light to a central point. The top surface of each facet of a Fresnel lens retains a curvature associated with a corresponding spherical or curved lens. In contrast, the surface of each facet 383 of output lens 275 does not retain a curvature associated with a corresponding curved lens, but rather uses prismatic effects to refract light. Thus, for example, the surfaces of a facet 383 of output lens 275 may be flat or approximately flat. Accordingly, output lens 275 changes the input profile of incoming light by shifting a portion of the incoming light toward the periphery, leaving less laser energy in the center of the incoming beam profile and creating an annular distribution of radiation emissions.

FIG. 3B shows a cross-section of the output lens 275 of FIG. 3A. Output lens 275 comprises a first surface 322 on which are located facets 383, including facets 383-I, 383-A, 383-B, and 383-O. Output lens 275 also comprises a second surface 328. Output lens 275 has a thickness T and a diameter D. In the embodiment of FIG. 3B, facets 383 are arranged concentrically around a central axis 379-A.

Figure 3C:
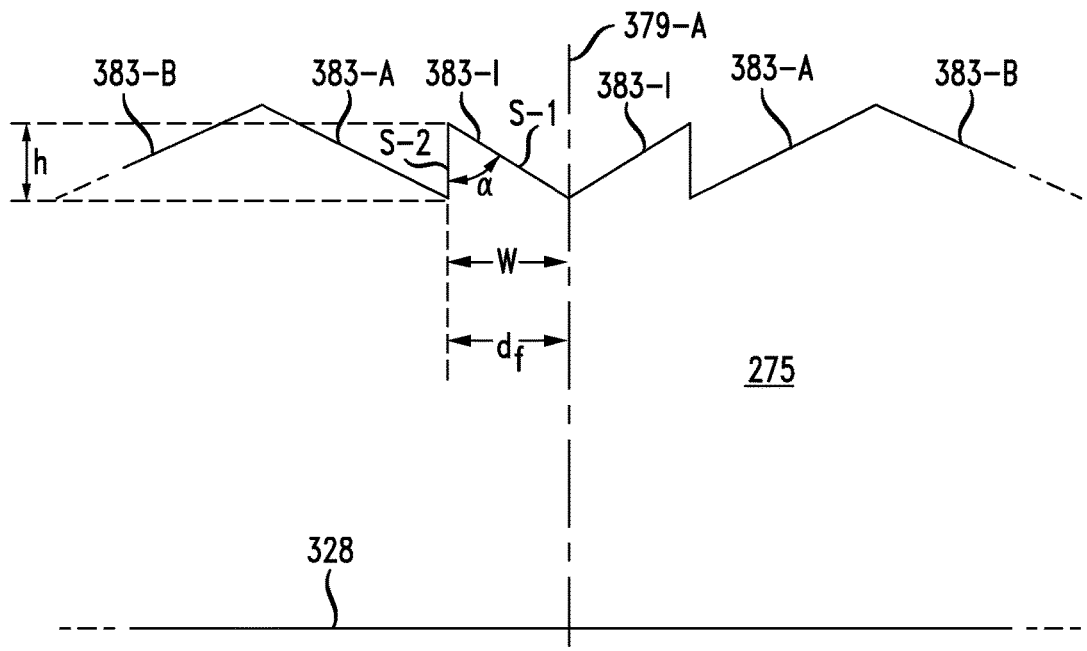
FIG. 3C shows several facets of the output lens of FIGS. 3A-3B.

FIG. 3C shows inner facets 383-I, 383-A, and 383-B of the embodiment of FIG. 3B in further detail. As discussed above, facets 383-I, 383-A, and 383-B are arranged concentrically around central axis 379-A. In other embodiments, facets 383 may be arranged differently.

Each facet 383 is defined by characteristics including a facet height, a facet width, and a facet angle. For example, facet 383-I has an inner, sloping side S-1, an outer, vertical side S-2, a facet height h, a facet width W, and a facet angle α. In this discussion, the inner side of a facet is the side closest to central axis 379-A and the outer side is the side of the facet that is farthest from central axis 379-A. While in FIG. 3C, the inner side S-1 of facet 383-I is sloping and the outer side S-2 is vertical, other facets may be constructed differently. For example, facet 383-O (shown in FIG. 3B) has a sloping outer side. In some case, such as in the case of facets 383-A and 383-B, where a facet having a sloping inner side is adjacent to a facet having a sloping outer side, the facets may be joined and not have a vertical side. In other embodiments, a facet may have two sloping sides and no vertical side.

In the illustrative embodiment, the surface of side S-1 and the surface of side S-2 are flat or approximately flat. The surfaces of other facets are also flat or approximately flat.

In this discussion, the facet angle α is the angle between side S-1 and side S-2. For a particular facet, the value of facet angle α is negative if the inner side S-1 of the facet is sloping; facet angle α is positive if the outer side S-2 is sloping.

Each facet is further defined by its distance from the central axis of the output lens. Referring to FIG. 3C, facet 383-A is located at a distance df from central axis 379-A. More specifically, distance df represents the distance between central axis 379-A and the innermost point of facet 383-A.

The height of facets 383 may vary. Referring to FIG. 3C, facet 383-I is defined by a height h. In the embodiment of FIG. 3B, the height of inner facet 383-I is smaller than the height of outer facet 383-O. In one embodiment, the height of a facet 383 varies based on the distance of the facet from the center line 379 of output lens 275. For example, the height of facets 383 may increase uniformly from inner facet 383-I to outer facet 383-O. In other embodiments, the height of facets 383 may vary non-uniformly, for example, according to a selected linear or non-linear function, or based on other factors.

Referring to FIG. 3C, facet 383-I has a facet width W. The facet width W may vary. In one embodiment, facet width is selected to be as small as possible commensurate with manufacturing considerations of the machining/molding processes used.

The number of facets 383 may vary as well. While FIGS. 3A and 3B show an embodiment having a particular number of facets, in other embodiments, output lens 275 may have a different number of facets than that shown.

In various embodiments, thickness T and diameter D of output lens 275 may vary. For example, output lens 275 may have a thickness between 1 to 5 millimeters, and a diameter D of approximately 25 millimeters. In other embodiments, output lens 275 may have other thicknesses and other diameters.

Characteristics of output lens 275, and characteristics of facets 383, may be selected empirically to function optimally with a given slit lamp assembly. For example, in one embodiment, the diameter D and thickness T of output lens 275, the number of facets, and the facet height, facet width, facet distance, the facet angles of facets 383, etc., may be determined empirically based on characteristics of slit lamp assembly 280, such as the size and location of one or more lenses in the slit lamp assembly 280, and on the size of the light collection area. Output lens 275 may also be designed and manufactured based on the size and shape of a desired temperature profile to be delivered to a target zone. In another example, characteristics of facets 383, such as facet angles, etc., may be selected empirically according to the "best focal distance" required and the refractive index of the material used to manufacture the lens. In other examples, characteristics of facets 383, such as facet angles, etc., may be selected based on working distance, the size of a desired spot or ring, available manufacturing tolerances, the number and spacing of the grooves on output lens 275, etc.

Figure 3D:
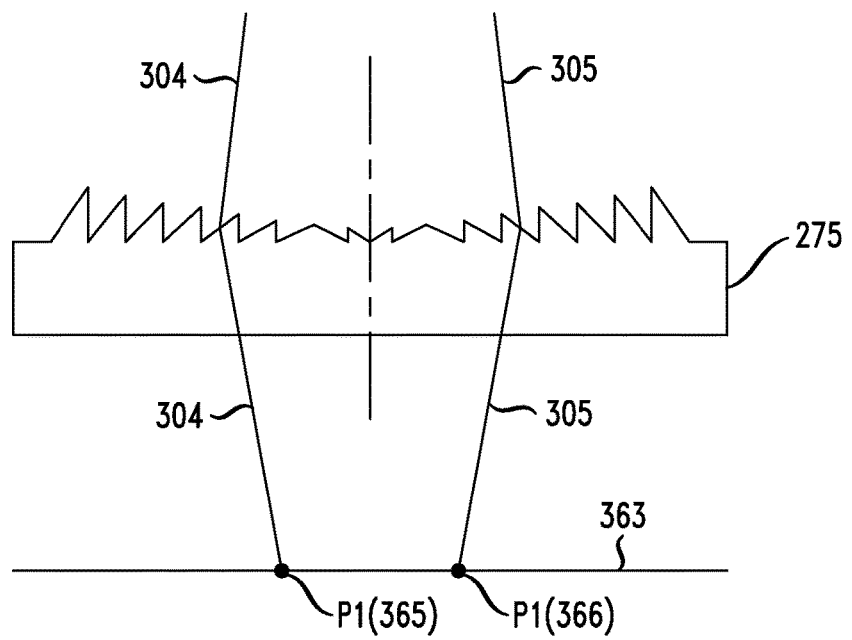
FIG. 3D shows an output lens refracting and focusing beams of radiation onto a focal plane in accordance with an embodiment.

Output lens 275 may accordingly be designed and manufactured to refract incoming radiation and to produce an annular illumination pattern at a selected focal plane associated with the lens. FIG. 3D shows output lens 275 refracting and focusing beams of radiation 304, 305 onto a focal plane 363 in accordance with an embodiment. In this example, beams 304 and 305 intersect focal plane 363 at points P1 (365) and P2 (366), respectively.

Figure 4:
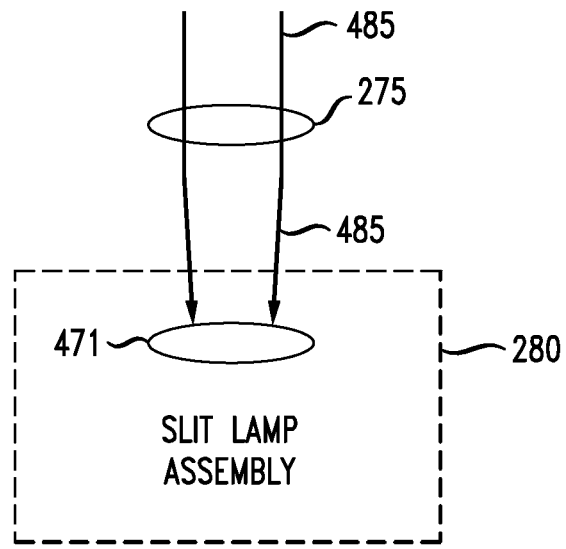
FIG. 4 shows an output lens and an optical component of a slit lamp in accordance with an embodiment.

FIG. 4 shows output lens 275 and an optical component of slit lamp 471 in accordance with an embodiment. In this example, radiation 485 is received, refracted, and emitted by output lens 275. Optical component 471 (such as a lens or mirror) within slit lamp 280 receives radiation 485. Optical component 471 may be disposed at the focal plane associated with output lens 275, for example. Optical component 471 may further refract, reflect or otherwise manipulate the radiation.

Table 1 includes data defining an embodiment of output lens 275. Each row of Table 1 represents, and includes data defining, one facet of the output lens. Specifically, Table 1 comprises three columns specifying (1) a facet angle α, expressed in degrees, (2) a facet distance df defining a distance between the central axis of the output lens and the innermost point of the facet, and (3) the facet angle α, expressed in arcseconds.

In the embodiment defined in Table 1, the two innermost facets have negative facet angles and therefore have sloping inner sides. In other embodiments, facet angles may be selected and arranged in any combination. For example, in some embodiments, all facets may have negative facet angles. In other embodiments, all facets may have positive facet angles. In other embodiments, the facets of the output lens may have any combination of positive and negative facet angles.

TABLE 1

| Facet Angle α (degrees) | Facet Distance $d_f$ (mm) | Facet Angle α (arcseconds) |
| --- | --- | --- |
| −0.117 | 0 | −419.49 |
| −0.039 | 0.2 | −139.83 |
| 0.039 | 0.4 | 139.83 |
| 0.117 | 0.6 | 419.49 |
| 0.194 | 0.8 | 699.15 |
| 0.272 | 1 | 978.80 |
| 0.350 | 1.2 | 1258.45 |
| 0.427 | 1.4 | 1538.08 |
| 0.505 | 1.6 | 1817.71 |
| 0.583 | 1.8 | 2097.31 |
| 0.660 | 2 | 2376.91 |
| 0.738 | 2.2 | 2656.48 |
| 0.816 | 2.4 | 2936.04 |
| 0.893 | 2.6 | 3215.57 |
| 0.971 | 2.8 | 3495.07 |
| 1.048 | 3 | 3774.55 |
| 1.126 | 3.2 | 4054.00 |
| 1.204 | 3.4 | 4333.42 |
| 1.281 | 3.6 | 4612.81 |
| 1.359 | 3.8 | 4892.16 |
| 1.437 | 4 | 5171.47 |
| 1.514 | 4.2 | 5450.74 |
| 1.592 | 4.4 | 5729.98 |
| 1.669 | 4.6 | 6009.16 |
| 1.747 | 4.8 | 6288.30 |
| 1.824 | 5 | 6567.39 |
| 1.902 | 5.2 | 6846.44 |
| 1.979 | 5.4 | 7125.42 |
| 2.057 | 5.6 | 7404.36 |
| 2.134 | 5.8 | 7683.23 |
| 2.212 | 6 | 7962.05 |
| 2.289 | 6.2 | 8240.81 |
| 2.367 | 6.4 | 8519.50 |
| 2.444 | 6.6 | 8798.13 |
| 2.5 | 6.8 | 9076.69 |
| 2.599 | 7 | 9355.18 |
| 2.676 | 7.2 | 9633.60 |
| 2.753 | 7.4 | 9911.94 |

TABLE 1-continued

| Facet Angle α (degrees) | Facet Distance $d_f$ (mm) | Facet Angle α (arcseconds) |
|---|---|---|
| 2.831 | 7.6 | 10190.21 |
| 2.908 | 7.8 | 10468.40 |

Figure 5:
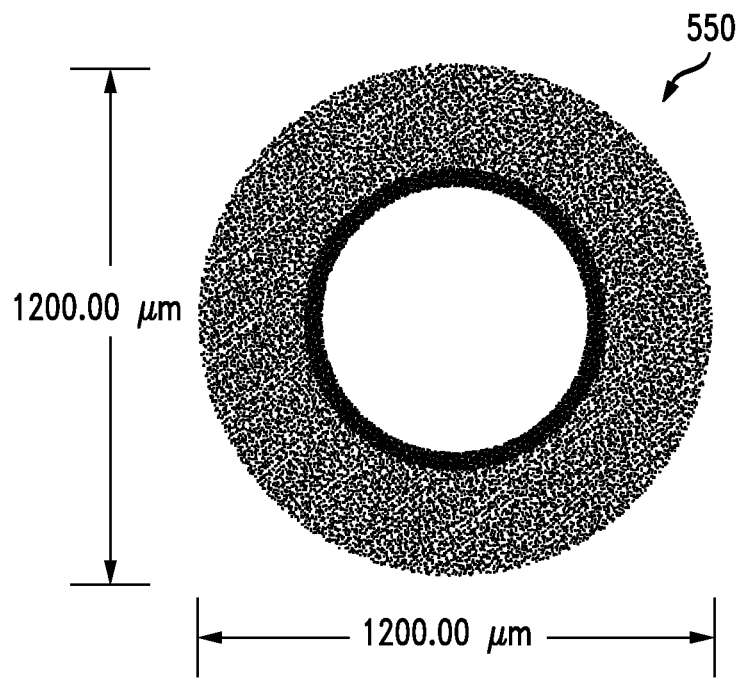
FIG. 5 shows a simulation of an annular illumination pattern produced by an output lens in accordance with an embodiment.

FIG. 5 shows a simulation of an annular illumination pattern (or profile) 550 produced by the output lens defined in Table 1. Specifically, FIG. 5 is a computer simulation of an image that may be captured at a focal plane approximately 290 millimeters from the output lens defined in Table 1. The annular profile 550 of FIG. 5 is shown on a grid representing a 1.2 mm×1.2 mm square. As shown, the output lens defined in Table 1 generates an annular profile having a diameter of approximately 1 millimeter.

Figure 6:
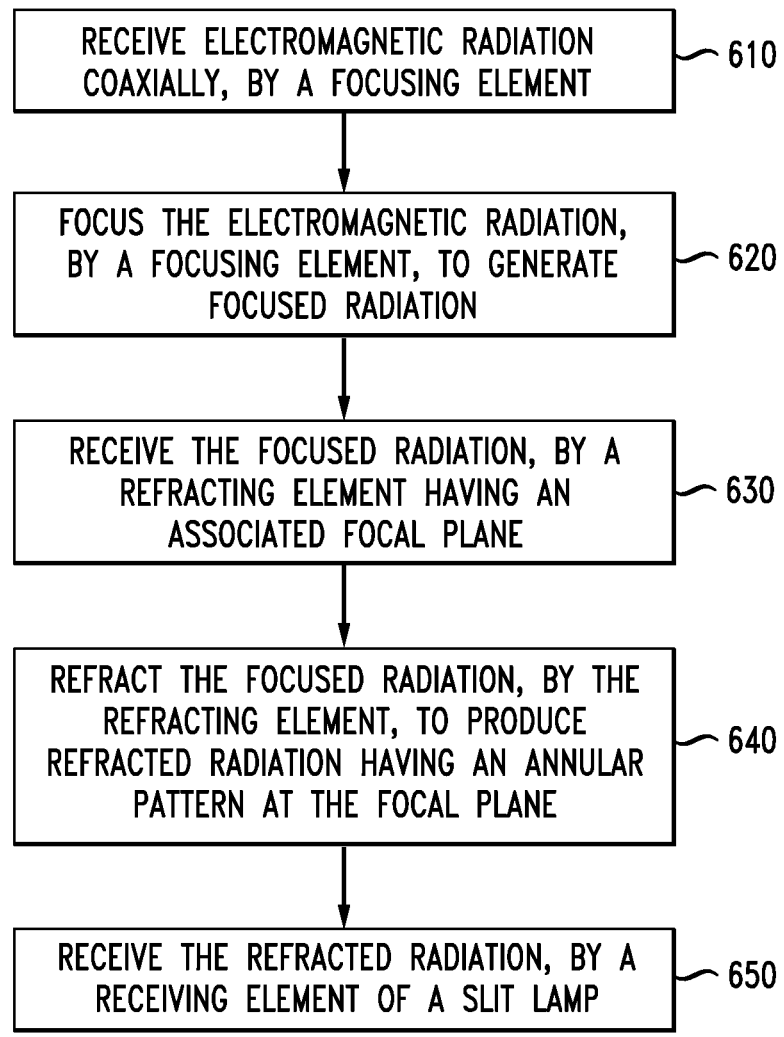
FIG. 6 is a flowchart of a method of delivering radiation to a slit lamp assembly in accordance with an embodiment.

FIG. 6 is a flowchart of a method of delivering radiation to a slit lamp assembly in accordance with an embodiment. FIG. 6 is discussed below with reference also to FIG. 2.

At step 610, electromagnetic radiation is received coaxially by a focusing element. Referring to FIG. 2, electromagnetic radiation source 210 generates radiation, which is received coaxially by input lens 225.

At step 620, the electromagnetic radiation is focused by a focusing element to generate focused radiation. Input lens 225 focuses the radiation; the focused radiation is received at first fiber end-face 237 of fiber 240. Fiber 240 carries the focused radiation and emits the focused radiation via second fiber end-face 243.

At step 630, the focused radiation is received by a refracting element having an associated focal plane. Output lens 275 receives the focused radiation emitted via second fiber-end face 243.

At step 640, the focused radiation is refracted, by the refracting element, to produce refracted radiation having an annular pattern at the focal plane. In the manner discussed above, output lens 275 refracts the radiation received from second fiber-end face 243 and generates an annular illumination pattern at an associated focal plane.

At step 650, the refracted radiation is received by a receiving element of a slit lamp. An optical element of slit lamp assembly 280 (such as element 471 shown in FIG. 4) receives the refracted radiation emitted by output lens 275. The radiation may be further focused, refracted, and manipulated by elements of slit lamp assembly 280. Slit lamp assembly 280 subsequently directs the radiation into a patient's eye.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system comprising:
a focusing element that:
receives electromagnetic radiation coaxially, the electromagnetic radiation coaxially received being independent of a selected acute input angle associated with an input beam from a source of the electromagnetic radiation; and
focuses the electromagnetic radiation to generate focused radiation;
a refracting element having an associated focal plane, wherein the refracting element comprises a first surface, a central point, and a plurality of facets located on the first surface and arranged concentrically around the central point, each facet having (i) a respective height that varies based on a distance from the central point, (ii) a respective variable width; and (iii) a respective variable facet angle, the respective variable facet angle being either positive or negative, and wherein each facet has a respective surface such that the plurality of facets refract the focused radiation using prismatic effects, and one or more of the respective surfaces of the plurality of facets is an approximately flat surface, and the refracting element having a first facet of the plurality of facets having a positive facet angle adjacent to and joined with a second facet of the plurality of facets having a negative facet angle, such that the refracting element:
receives the focused radiation;
refracts, using the prismatic effects of the plurality of facets, the focused radiation by changing an incoming beam profile of the electromagnetic radiation received through shifting a portion of the electromagnetic radiation received toward a periphery of the refracting element to produce refracted radiation having an annular pattern at the focal plane; and
a slit lamp comprising a receiving element that receives the refracted radiation.

2. The system of claim 1, further comprising:
an electromagnetic radiation source.

3. The system of claim 1, further comprising a fiber having a first end and a second end for:
receiving the focused radiation emitted by the focusing element via the first end; and
emitting the focused radiation via the second end;
wherein the refracting element receives the focused radiation emitted via the second end.

4. The system of claim 1, wherein
the first facet has a first sloping surface, a first vertical surface, and the positive facet angle associated with a first angle between the first sloping surface and the first vertical surface; and
the second facet has a second sloping surface, a second vertical surface, and the negative facet angle associated with a second angle between the second sloping surface and the second vertical surface.

5. An imaging system comprising a plurality of lenses, the system comprising:
a first lens of the plurality of lenses that:
receives input light coaxially, the input light coaxially received being independent of a selected acute input angle associated with an input beam from a source of the input light; and
focuses the light to produce focused light;
a second lens of the plurality of lenses, the second lens comprising a first surface, a central point, and a plurality of facets located on the first surface and arranged concentrically around the central point, each facet having (i) a respective height that varies based on a distance from the central point, and wherein each facet has a respective surface such that the plurality of facets refract the focused light using prismatic effects, (ii) a respective variable width; and (iii) a respective variable facet angle, the respective variable facet angle being either positive or negative, and one or more of the respective surfaces of the plurality of facets is an approximately flat surface, and the second lens having a first facet of the plurality of facets having a positive facet angle adjacent to and joined with a second facet of the plurality of facets having a negative facet angle, such that the second lens changes an incoming beam profile of the input light received by shifting a portion of the input light received toward a periphery of the second lens, and wherein the second lens having an associated focal plane that refracts, using the prismatic effects of the plurality of facets, the focused light to produce refracted light having an annular illumination pattern at the focal plane.

6. The imaging system of claim 5, wherein
the first facet has a first sloping surface, a first vertical surface, and the positive facet angle associated with a first angle between the first sloping surface and the first vertical surface; and
the second facet has a second sloping surface, a second vertical surface, and the negative facet angle associated with a second angle between the second sloping surface and the second vertical surface.

7. The imaging system of claim 6, wherein the source is a slit lamp.

8. The imaging system of claim 6, wherein the slit lamp comprises an optical element that receives the refracted light at the focal plane.

9. The imaging system of claim 6, the annular illumination pattern, produced from the second lens, is created as a result of leaving less radiation energy in a center of the incoming beam profile.

10. The imaging system of claim 5, further comprising a fiber that
receives the focused light at a first end; and
emits the focused light via a second end.

11. A method comprising:
receiving electromagnetic radiation coaxially, the electromagnetic radiation coaxially received being independent of a selected acute input angle associated with an input beam from a source of the electromagnetic radiation, by a focusing element;
focusing the electromagnetic radiation to generate focused radiation;
receiving the focused radiation, by a refracting element comprising a first surface, a central point, and a plurality of facets located on the first surface and arranged concentrically around the central point, each facet having (i) a respective height that varies based on a distance from the central point, (ii) a respective variable width; and (iii) a respective variable facet angle, the respective variable facet angle being either positive or negative, and the refracting element having a first facet of the plurality of facets having a positive facet angle adjacent to and joined with a second facet of the plurality of facets having a negative facet angle, wherein each facet has a respective surface such that the plurality of facets refract the focused radiation using prismatic effects, and one or more of the respective surfaces of the plurality of facets is an approximately flat surface;
refracting the focused radiation, by the refracting element using the prismatic effects of the plurality of facets, to produce refracted radiation having an annular pattern at a focal plane associated with the refracting element;
providing the refracted radiation to a slit lamp; and
changing, by the refracting element, an incoming beam profile of the electromagnetic radiation received by shifting a portion of the electromagnetic radiation received toward a periphery of the refracting element.

12. The method of claim 11, wherein:
the first facet has a first sloping surface, a first vertical surface, and the positive facet angle associated with a first angle between the first sloping surface and the first vertical surface; and
the second facet has a second sloping surface, a second vertical surface, and the negative facet angle associated with a second angle between the second sloping surface and the second vertical surface.

13. A refracting element having an associated focal plane, the refracting element comprising:
a plurality of facets arranged concentrically with respect to a central point, each facet having a respective surface such that the plurality of facets use prismatic effects to refract incoming radiation, each facet further comprising:
a respective height that varies based on a distance from the central point;
a respective variable width;
a respective variable facet angle, the respective variable facet angle being either positive or negative;
an approximately flat surface that receives the incoming radiation and refracts the incoming radiation using the prismatic effects of the plurality of facets such that the refracting element changes an incoming beam profile of the incoming radiation received by shifting a portion of the incoming radiation received toward a periphery of the refracting element; and
wherein the refracting element has a first facet of the plurality of facets having a positive facet angle adjacent to and joined with a second facet of the plurality of facets having a negative facet angle, and the refracted radiation has an annular illumination pattern at a focal plane associated with the refracting element.

* * * * *